United States Patent [19]

Langer

[11] 4,323,075
[45] Apr. 6, 1982

[54] BATTERY FAILURE COMPENSATION FOR A POWER SUPPLY USED IN AN IMPLANTABLE DEFIBRILLATOR

[75] Inventor: Alois A. Langer, Pittsburgh, Pa.

[73] Assignee: Mieczyslaw Mirowski, Owings Mills, Md.

[21] Appl. No.: 53,733

[22] Filed: Jul. 2, 1979

[51] Int. Cl.³ .............................................. A61N 1/36
[52] U.S. Cl. .............................................. 128/419 D
[58] Field of Search ....................... 128/419 D, 419 PS

[56] References Cited

U.S. PATENT DOCUMENTS

| | | | |
|---|---|---|---|
| 3,614,954 | 10/1971 | Mirowski et al. | 128/419 D |
| 3,783,877 | 1/1974 | Bowers | 128/419 PS |
| 3,857,398 | 12/1974 | Rubin | 128/419 D |
| 3,952,750 | 4/1976 | Mirowski et al. | 128/419 D |

FOREIGN PATENT DOCUMENTS 474271  8/1969  Switzerland ................... 128/419 PS Primary Examiner—William E. Kamm
Attorney, Agent, or Firm—Fleit & Jacobson

[57] ABSTRACT

A fully implantable power supply for use with or in a fully implantable defibrillator, which has a fibrillation detector in circuit with the power supply and a power inverter switchably in circuit with the power supply. The power supply comprises an energy source which includes a plurality of batteries arranged in series, each of the batteries having a pair of output terminals, each of the batteries producing a multilevel voltage across its pair of output terminals, the voltage being at a first level when the battery is fully charged and dropping to a second level at some point during the discharge of the battery. Circuitry in the form of a plurality of unidirectional conducting devices is provided for creating a first conductive path between the serially-connected batteries and the fibrillation detector, and a second conductive path between the inverter and the batteries that are producing the first level of voltage.

15 Claims, 2 Drawing Figures

BATTERY FAILURE COMPENSATION FOR A POWER SUPPLY USED IN AN IMPLANTABLE DEFIBRILLATOR

BACKGROUND OF THE INVENTION

1. Field of the Invention

This invention relates to power supplies for life assisting devices, in general, and to an implantable power supply for use with an implantable defibrillator, in particular.

2. Description of the Prior Art

Great strides are presently being made to develop an automatic, fully implantable ventricular defibrillator. See, for example, U.S. Pat. Nos. Re. 27,652 and Re. 27,757, where the first concept of the automatic implantable ventricular defibrillator is described. Recent advances have also been made in enhancing the reliability of fibrillation detectors. In this latter regard, see copending U.S. Pat. No. 4,184,493 and U.S. Pat. No. 4,202,340, each filed on Feb. 15, 1978. Furthermore, as outlined in copending U.S. Pat. No. 4,164,946, filed on May 27, 1977, steps have been taken to improve the reliability of the implanted defibrillator by the provision of circuitry which interrogates the implanted electronics to verify proper operation before a defibrillation shock is delivered.

Notwithstanding the substantial steps which have been taken to develop the automatic, fully implantable defibrillator and to insure the operation of the sensing and defibrillating circuitry, it must not be forgotten that the implantable defibrillator is in its infancy.

In an implantable defibrillator, a fibrillation detecting circuit, operatively associated with the heart of a recipient, detects a fibrillation episode, and, in response thereto, activates a power inverter. When activated, the power inverter directs energy from an energy source, such as a battery, to an energy storage device, such as a storage capacitor. When the storage capacitor is fully charged, additional circuitry contained in the defibrillator releases the energy stored in the storage capacitor into the heart of the recipient as a defibrillating shock.

In the implantable defibrillator discussed above, the detection circuit and the charging circuit are powered by two extended-life batteries connected in series. Still, it is possible for one of the batteries to become discharged, while the other battery may still be far from depleted. In such an instance, the prior circuit design would not permit continued operation of both the detection and the charging circuits.

The problem of battery failure is also present in the field of cardiac pacemakers and other implantable body organ stimulators. In these other fields, it has been proposed that the battery depletion problem can be overcome by connecting fewer batteries in series, connecting series groups in parallel, using diode "or" connections, and using voltage doubler and tripler circuits for producing sufficient voltage for effective device operation.

None of these alternative arrangements offers a solution to the unique problem associated with implantable defibrillators; namely, that of assuring continued operation of the fibrillation detecting circuit and the power inverter over the full life of the batteries because the inverter draws several orders of magnitude more current than the detecting circuit.

SUMMARY OF THE INVENTION

The present invention relates to an implantable energy source or power supply for use in or with an implantable defibrillator. In a preferred embodiment, the energy source provides power to a fibrillation detector, in circuit with the power supply, and to an inverter, ready to be switched in circuit with the power supply. The power supply comprises a plurality of batteries arranged in series, each of the batteries having a pair of output terminals, and each of the batteries producing a multilevel voltage across its pair of output terminals due to two distinct chemical reactions being possible. The voltage produced by each of the batteries is at a first level of magnitude, when the particular battery is fully charged, and drops to a second level at some point during the discharge of the battery. (At its second level, the battery may be considered to be "dead" since, in a simple series connection, a battery at its second level is not capable of supporting the current necessary to run an inverter and, thus, an implanted device would not function.) In the modified circuit, a diode-arrangement is provided for creating a first conductive path between serially connected batteries and the fibrillation detector, and a second conductive path between the inverter and the batteries that are producing the first level of voltage.

Normally, the fibrillation detector requires a first level of power that is at least the product of the sum of the second level voltages and the current generated by the batteries when they are at the second voltage level. Normally, the inverter requires a second level of power which is at least a product of the first level of voltage of any one of the batteries and the current generated by the same battery when it is at the first voltage level.

The pair of output terminals associated with each battery comprises a positive terminal and a negative terminal. The negative terminal of the first battery is connected to the positive terminal of the second battery to form a connection point. The diode arrangement includes first and second diodes, the anode of the first diode and the cathode of the second diode being connected to the connection point. The cathode of the first diode is connected to the positive terminal of the first battery, while the anode of the second diode is connected to the negative terminal of the second battery.

Thus, it is an object of the present invention to provide a fully implantable defibrillator which is less prone to premature power source failure.

It is another object of the present invention to provide an implantable power source in which the hazard of battery venting is prevented.

It is yet another object of the present invention to provide an energy source in which the batteries constituting the energy source are not susceptible to reverse charging.

It is still another object of the present invention to provide a simple circuit for use with batteries producing multilevel voltages for powering an implantable defibrillator.

It is a further object of the present invention to provide an implantable energy source for use with implantable utilization devices.

Other objects and advantages of this invention will further become apparent hereinafter and in the drawings.

DETAILED DESCRIPTION OF THE DRAWINGS

Figure 1:
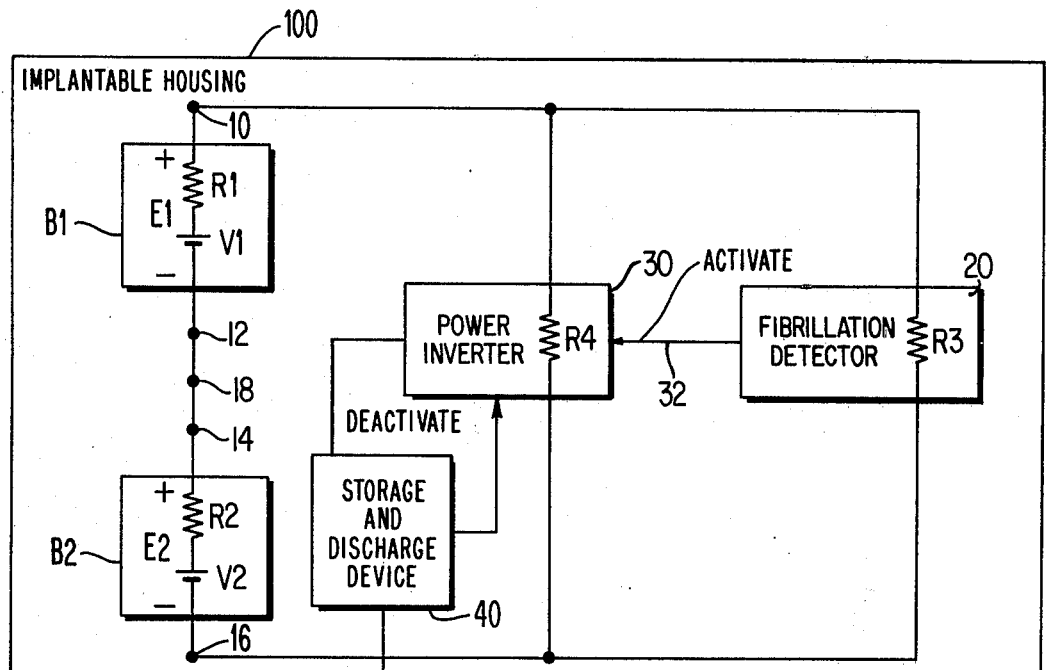
FIG. 1 is a schematic diagram of a portion of an implantable defibrillator using a prior art energy source.

With reference to FIG. 1, the prior art problems associated with powering the fibrillation detector and the power inverter of an implantable defibrillator will be discussed. FIG. 1 discloses a basic circuit confined within a conventional implantable housing 100 of known structure for implantation within the human body. The circuit includes a fibrillation detector 20, whose load characteristic is represented by a resistor R3 is powered by a pair of batteries B1 and B2 connected in series. Resistors R1 and R2 schematically represent the internal resistances associated with batteries B1 and B2, respectively.

Each of the batteries contains a pair of output terminals: for battery B1, these are positive terminal 10 and negative terminal 12, and for battery B2, these are positive terminal 14 and negative terminal 16. The negative terminal 12 of battery B1 is connected to the positive terminal 14 of battery B2 at connection point 18. Voltages V1 and V2 represent the voltages produced by batteries B1 and B2, respectively. Each of the batteries B1 and B2 produces an electromotive force E1 and E2, respectively. By way of illustration, the electromotive force E1 for battery B1 is equal to the voltage V1 minus internal losses caused by a current passing through internal resistance R1, when the battery is in a complete circuit.

Each of the batteries B1 and B2 characteristically produces a multilevel voltage E1 and E2, respectively, across its associated output terminals, and the values of resistance change dramatically between levels. The voltage E1 or E2 (hereinafter sometimes referred to as E) is at a first level of approximately 3.4 volts with low internal resistance when the battery is fully charged, and drops to a second level of approximately 2.2 volts with high internal resistance at some point during the discharge of the battery. This operational characteristic of the battery is provided through a battery having a multiple valence electron structure. One such battery employs Lithium-Vanadium Pentoxide chemistry. When fully charged, the battery produces an electromotive force E of approximately 3.4 volts and possesses a high-current drain capability. As the battery is depleted of 3.4-volt valence electrons, the battery then produces an electromotive force E of 2.2 volts, but with only a low-current drain capability, which is caused by the release of 2.2-volt valence electrons and can be modeled as an increase of IR losses within the battery.

The fibrillation detector 20 appears as a high resistance load to the batteries and is operative at a low current. By design, the power required to make the fibrillation detector 20 operable is, at least, the product of the sum of the second level voltages, and the current generated by the batteries when they are at said second voltage level. Therefore, even if one battery, say B1, has discharged so that it is now operating at the 2.2 volt level, the series connection is still capable of generating sufficient current and voltage to satisfy the needs of the fibrillation detector. In an implantable defibrillator, the fibrillation detector 20, operatively associated with the heart, detects a fibrillation episode, and, in response thereto, activates the power inverter 30.

Upon detection of a fibrillation, a power inverter 30 is introduced into the circuit by being connected to terminals 10 and 16 in response to an activation signal received from the fibrillation detector on line 32. The power inverter remains in the circuit until it has directed energy from the batteries B1 and B2 to an energy storage and discharge device 40, which may comprise a storage capacitor and additional circuitry for releasing, via a known shock delivery probe 60, the energy stored in the storage capacitor into the heart of the recipient as a defibrillating shock. When the storage capacitor is fully charged, the energy storage and discharge device 40 deactivates and removes the inverter 30 from the circuit. Thus, the power inverter 30 is intermittently in circuit with the batteries B1 and B2. The load characteristic of the power inverter is schematically represented as resistive load R4. The inverter 30, characteristically, has a low resistive load and requires a large current for operation. By design, the power inverter 30 requires a second level of power which is at least the product of the first level of voltage of any one of the batteries B1 of B2 and the current generated by the battery when it is at the first voltage level. When any one of the batteries is operating at the first voltage level, 3.4 volts, it is capable of providing the inverter with power necessary for the inverter to carry out its function.

When either of batteries B1 or B2 drops to the second level of voltage, 2.2 volts, that battery is no longer able to support the current drain needed by the power inverter. In this case the inverter would not run; also, the possibility exists of a reverse-charging condition which leads to polarization and venting within the low voltage battery.

Figure 2:
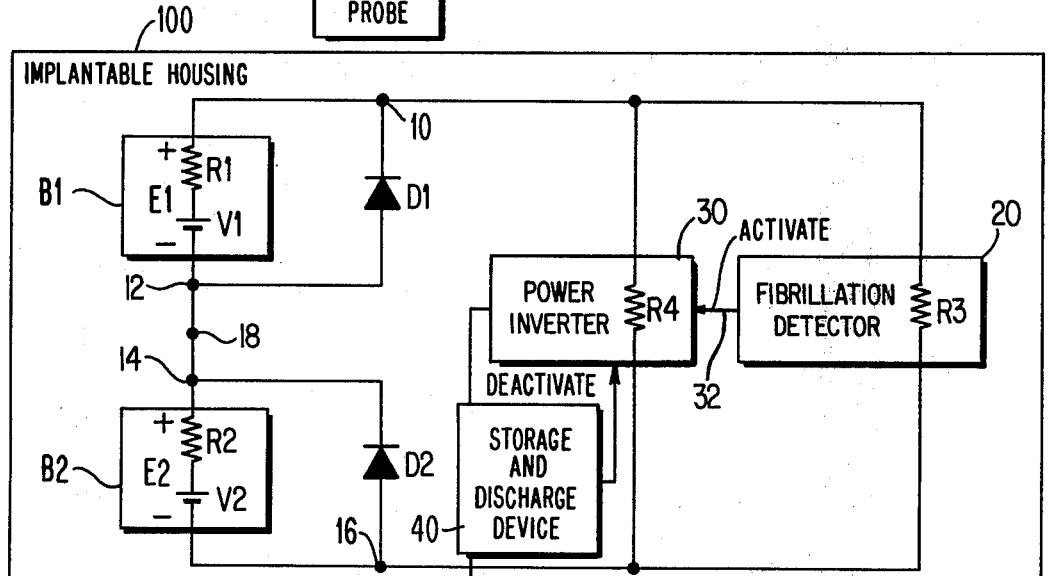
FIG. 2 is a schematic diagram of a portion of an implantable defibrillator embodying the subject invention.

FIG. 2 is a schematic diagram useful in describing a preferred embodiment of the subject invention. In this regard, it should be noted that the elements, which are the same as those in FIG. 1, are similarly numbered and the distinguishing features only will be described. A diode D1, typically of the Schottky variety, has a forward voltage drop of approximately 0.4 volts, diode D1 has its cathode connected to the positive terminal 10 of battery B1 and its anode connected to the negative terminal 12 of battery B1. A second diode D2, also typically of the Schottky type, has a forward voltage drop of approximately 0.4 volts. Diode D2 has its cathode connected to the positive terminal 14 of battery B2 and its anode connected to the negative terminal of battery B2. With reference to FIG. 2, when batteries B1 and B2 are operating at their first voltage level, 3.4 volts, they are capable of providing sufficient current to the fibrillation detector 20. In this mode of operation, the diodes D1 and D2 remain inoperative. When the power inverter 30 is introduced into the circuit as shown in phantom, the diodes D1 and D2 still remain inoperative, batteries B1 and B2 being capable of delivering the required level of current to satisfy the requirements of the power inverter.

When one of the batteries drops to its second level of voltage, 2.2, volts, and the inverter is started, the diodes come into play. Assume that battery B2 is operating at its second level of voltage. Under this condition battery B2 has a current drain capability which is not sufficient to sustain the current required by the inverter 30. This is caused mainly by the increase of the internal resistance R2 which leads to a voltage drop opposite to the initial polarity of the battery B2 when current is forced to flow by the second "good" battery B1. Under these circumstances, diode D2 becomes conductive (preventing the reverse potential across battery B2) to create a current path between the inverter 30 and battery B1, which has a current drain characteristic capable of providing the necessary current to the inverter. As stated before, the inverter 30 has been designed so that its power requirement is met by the voltage generated by battery B1 coupled with the current drain characteristic of that battery.

Obviously many modifications and variations of the present invention are possible in light of the above teachings, and it is therefor to be understood that within the scope of the appended claims, the invention may be practiced otherwise than as specifically described.

I claim:

1. A fully implantable power supply for use in a fully implantable defibrillator having an implantable housing, a fibrillation detector for detecting fibrillation of the heart of a recipient, an energy storage and discharge device for storing and releasing defibrillation energy into the heart of the recipient and an inverter for charging the energy storage and discharge device in response to detection of fibrillation by the fibrillation detector, the inverter requiring a first level of power to be operational and the fibrillation detector requiring a second level of power different from said first level of power to be operational, said power supply comprising:
   implantable battery means positioned within said implantable housing, said battery means including a plurality of batteries arranged in series, each of said batteries having a pair of output terminals, each of said batteries producing a distinctly multilevel voltage across its pair of output terminals, said voltage being at a first level when the battery is fully charged and dropping to a second level at some point during the discharge of the battery; and
   implantable circuit means positioned within said implantable housing, said circuit means for creating a first conductive path betwen said serially-connected batteries and said fibrillation detector to provide said fibrillation detector with said second level of power, and for creating a second conductive path between said inverter and said battery means by placing only the batteries operating at said first level voltage in said second conductive path, and excluding the remaining batteries from said second conductive path to provide said inverter with said first level of power.

2. The power supply of claim 1, wherein said plurality of batteries is two batteries, and the pair of output terminals of each battery comprises a positive terminal and a negative terminal, the positive terminal of one battery being connected to the negative terminal of the other battery to form connection point.

3. The power supply of claim 1, wherein said first voltage level is approximately 3.4 volts and second voltage level is approximately 2.2 volts.

4. The power supply of claim 2, wherein said circuit means comprises:
   first and second unidirectional conductive means, each of which has a certain forward voltage drop.

5. The power supply of claim 4, wherein said first and second unidirectional conductive means comprise, respectively, first and second diodes, the anode of said first diode and the cathode of said second diode being connected to said connection point, the cathode of said first diode being connected to the positive terminal of said other battery, and the anode of said second diode being connected to the negative terminal of said one battery.

6. The power supply of claim 5, wherein each diode is of the Schottky variety with a forward voltage drop of approximately 0.4 volts.

7. A fully implantable defibrillator comprising:
   an implantable housing;
   fibrillation detecting means within said housing for detecting fibrillation of the heart of a recipient, said detecting means requiring a first level of power to be made operational;
   energy storage and discharge means within said housing for storing and releasing defibrillating energy into the heart of a recipient;
   inverter means within said housing for charging the storage and discharge means in response to detection of fibrillation by said detecting means, said inverter requiring a second level of power different from said first level of power to be operational;
   battery means within said housing including a plurality of batteries arranged in series, each of said batteries having a pair of output terminals, each of said batteries producing a distinctly multilevel voltage across its pair of output terminals, said voltage being at a first level when the battery is fully charged and dropping to a second level at some point during the discharge of the battery; and
   circuit means within said housing for creating a first conductive path between said serially-connected batteries and said detecting means to provide said detecting means with said first level of power, and for creating a second conductive path between said inverter means and said battery means by placing only the batteries operating at said first level voltage in said second conductive path, and excluding the remaining batteries from said second conductive path to provide said inverter means with said second level of power.

8. The defibrillator of claim 7, wherein said first voltage level is approximately 3.4 volts, and said second voltage level is approximately 2.2 volts.

9. The defibrillator of claim 7 wherein said plurality of batteries is two batteries.

10. The defibrillator of claim 9, wherein said first level of power is, at least, the product of a current generated by one of said batteries when it is at said second level, and the sum of said second level voltages, and said second level of power is, at least, the product of the first level of voltage of any one of said batteries and the current generated by the same battery when it is at said first voltage level.

11. The defibrillator of claim 9, wherein said circuit means comprises first and second unidirectional conductive means.

12. The defibrillator of claim 11, wherein the pair of output terminals of each battery comprises a positive terminal and a negative terminal, the positive terminal of one battery being connected to the negative terminal of the other battery to form a connection point and said first and second unidirectional conductive means comprise, respectively, first and second diodes, the anode of said first diode and the cathode of said second diode being connected to said connection point, the cathode of said first diode being connected to the positive terminal of said other battery, and the anode of said second diode being connected to the negative terminal of said one battery.

13. The defibrillator of claim 12, wherein each diode has a forward voltage drop approximately equal to 0.4 volts.

14. A fully implantable defibrillator comprising:
an implantable housing;
battery means within said housing including a pair of batteries arranged in series, each of said batteries having a pair of output terminals, each of said batteries producing a distinctly multilevel voltage across its pair of output terminals, said voltage being at a first level when the battery is fully charged and dropping to a second level at some point during the discharge of the battery;
fibrillation detecting means within said housing for detecting fibrillation of the heart of a recipient, said detecting means having a current drain capable of being supplied by said batteries even when said batteries are operating at said second level voltage;
energy storage and discharge means within said housing for storing and discharging defibrillating energy into the heart of the recipient;
inverter means within said housing for charging said storage and discharge means in response to detection of fibrillation by said detecting means, said inverter means having a current drain capable of being supplied only by said batteries operating at said first level voltage; and
circuit means within said housing for creating a first conductive path between said serially-connected batteries and said detecting means for powering said detecting means, and for creating a second conductive path between said inverter means and said battery means, by placing only the batteries operating at said first level voltage in said second conductive path, and excluding the remaining batteries from said second conductive path.

15. The defibrillator of claim 14, wherein said fibrillation detecting means requiring a first level of power which is, at least, the product of a current generated by one of said batteries when it is at said second level voltage, and the sum of said second levels of voltage, and said inverter means requires a second level of power which is at least the product of the first level of voltage of any one of said batteries and the current generated by the same battery when it is at said first voltage level.

* * * * *